US011256087B2

(12) United States Patent
Tornèus et al.

(10) Patent No.: US 11,256,087 B2
(45) Date of Patent: Feb. 22, 2022

(54) HOLOGRAPHIC EYE IMAGING DEVICE

(71) Applicant: Tobii AB, Danderyd (SE)

(72) Inventors: Daniel Tornèus, Danderyd (SE); Peter Schef, Danderyd (SE); Magnus Arvidsson, Danderyd (SE); Peter Blixt, Danderyd (SE); Fredrik Mattinson, Danderyd (SE)

(73) Assignee: Tobii Ab, Danderyd (SE)

( * ) Notice: Subject to any disclaimer, the term of this patent is extended or adjusted under 35 U.S.C. 154(b) by 0 days.

(21) Appl. No.: 16/456,805

(22) Filed: Jun. 28, 2019

(65) Prior Publication Data

US 2020/0159012 A1    May 21, 2020

(30) Foreign Application Priority Data

Jun. 28, 2018 (SE) .................................... 1850813-5

(51) Int. Cl.
*G02B 27/00* (2006.01)
*G02B 5/32* (2006.01)
*G06F 3/01* (2006.01)

(52) U.S. Cl.
CPC ........... *G02B 27/0093* (2013.01); *G02B 5/32* (2013.01); *G06F 3/013* (2013.01)

(58) Field of Classification Search
CPC .. G02B 27/0093; G02B 27/0103; G02B 5/32; G02B 2027/0178; G06F 3/013; G02C 7/086; A61B 3/113
See application file for complete search history.

(56) References Cited

U.S. PATENT DOCUMENTS

| 5,980,041 A * | 11/1999 | Strachan ................ A61B 3/113 351/210 |
| 2010/0157400 A1* | 6/2010 | Dimov ................... G02B 5/188 359/13 |
| 2012/0194781 A1* | 8/2012 | Agurok .................. A61B 3/113 351/201 |
| 2018/0373046 A1* | 12/2018 | Alexander ......... G02B 27/0176 |

* cited by examiner

*Primary Examiner* — Alexander Eisen
*Assistant Examiner* — Kebede T Teshome
(74) *Attorney, Agent, or Firm* — Samuel I. Yamron

(57) ABSTRACT

The disclosure relates to an eye tracking device for tracking movements of an eye comprising, a viewing plane for displaying a projection of an image to the eye of a user, an image module placed on a same side of the viewing plane as the eye, at least one illuminator for illuminating the eye, a control unit adapted to receive an image captured by the image module, and calculate a viewing angle of the eye, a holographic optical element (HOE), wherein a HOE is placed between the eye and the viewing plane, wherein the image module is adapted to capture an image of the HOE, and wherein the HOE is adapted to direct at last a first portion of incident light reflected from the eye, in a first angle towards the image module, the first angle being different from an angle of the incidence of the incident light.

18 Claims, 6 Drawing Sheets

HOLOGRAPHIC EYE IMAGING DEVICE

CROSS-REFERENCE TO RELATED APPLICATION

The present application claims benefit to Swedish patent application No. 1850813-5, filed on Jun. 28, 2018, to Tornèus et al., entitled "Holographic Eye Imaging Device", and is hereby incorporated by reference in its entirety.

FIELD OF THE INVENTION

The present invention relates to an eye tracking device for tracking movements of an eye. More specifically, the disclosure relates to an eye tracking device for tracking movements of an eye according to the introductory parts of claim 1.

BACKGROUND ART

In eye tracking devices as e.g. eye tracking glasses, usually has a number of illuminating light sources for illuminating the eyes of a user with multiple glints per eye and one or two cameras for observing the eyes. The pupil of the eye is compared to the position to the glints in the eyes of the light sources to determine a viewing direction of the eye. The camera is usually placed at a large angle to the eyes, e.g. in the frame of the glasses. This is a not a good viewing angel. To make the viewing direction determination easier a number of light sources are used and a computing device is used to make the determination based on image analysis. Many light sources are however expensive and reduce the freedom of design of the eye tracking device. Powerful computing abilities are both expensive and energy consuming.

It is thus a need in the industry for cheaper eye tracking devices and/or eye tracking devices requiring less complex image analysis for determine the viewing direction of the eyes of a user.

SUMMARY

It is an object to mitigate, alleviate or eliminate one or more of the above-identified deficiencies in the art and disadvantages singly or in any combination and solve at least the above mentioned problem. According to a first aspect there is provided an eye tracking device for tracking movements of an eye comprising, a viewing plane for displaying a projection of an image to the eye of a user, an image module placed on a same side of the viewing plane as the eye, at least one illuminator for illuminating the eye, a control unit adapted to receive an image captured by the image module, and calculate a viewing angle of the eye, a holographic optical element, wherein a HOE is placed between the eye and the viewing plane, wherein the image module is adapted to capture an image of the HOE, and wherein the HOE is adapted to direct at last a first portion of incident light reflected from the eye, in a first angle towards the image module, the first angle being different from an angle of the incidence of the incident light. In this way the image module will be able to view an eye of a user directly from direction of the viewing plane that the user is watching. The image analysis is much simpler as the viewing angle of the image module is straight into the eye, saving computational power, cost and energy. The number of illuminators may also be reduced as the tracking is made simpler by the straight viewing angle of image module.

The viewing plane is the plane in which the image that the user is watching is placed.

The hologram of the HOE does not need to be placed directly on the viewing plane of the user. Especially for Virtual Reality (VR) headsets, a lens may be placed between the eye and the screen that places a virtual image on a comfortable distance a few meters away. In that case the HOE may be placed on the lens. It is, however, important that the HOE is placed between the viewing plane and the eye.

In Augmented Reality (AR) devices a projector may be placed at the side of the HOE or a prism so that the projector beam is directed towards the eye. The HOE should then be placed between any physical components and the eye.

According to some embodiments, the first HOE is adapted to direct a second portion of incident light reflected from the eye in a second angle towards the image module. This will split the image perceived by the image module into two overlapped images. This enables stereo imaging by separating the overlapped images using image analysis so that the depth of objects in the image can be determined.

According to some embodiments, the first portion of incident light has the first wavelength and the second portion of incident light has second wavelength, the eye tracking device further comprising a first illuminator emitting light of the first wavelength and a second illuminator emitting light of the second wavelength. Using two illuminators with different wavelengths that are split into overlapping images, the separation of the images is much easier and reduced to color separation.

According to some embodiments, further comprising a second HOE wherein the second HOE is adapted to direct incident light reflected from the eye in a second angle towards the image module and a second illuminator for illuminating the eye, wherein the first illuminator and second illuminator irradiate light of a first wavelength and a second wavelength, respectively, and wherein the first HOE is adapted to direct light the first wavelength but not the second wavelength and the second HOE is adapted to direct light the second wavelength but not the first wavelength. In that way the holograph in each HOE only need to reflect one wavelength, enabling simpler HOEs that possibly are cheaper.

According to some embodiments, the control unit is further adapted to control the illuminators such that only one illuminator is illuminating at the same time. By syncing the illumination timing with the recordings of the image module, stereo imaging may be achieved without any image analysis.

According to some embodiments, the control unit is further adapted to control the illuminators such that one illuminator is illuminating the majority of the time. The depth value is not needed for the majority of the time during eye tracking since the distance between the eye tracking device and the user's eyes normally is relatively fixed. It is enough to calculate the depth value at a longer interval thereby saving processing power and enhancing the speed of the eye tracking in the sense of temporal precision. The device could e.g. record ten images in the first wavelength for every image of the second wavelength.

According to some embodiments, the first HOE and the second HOE are combined in a photo polymer layer so as to make the assembly easier by reducing the number of components.

According to some embodiments, the first HOE and the second HOE are placed on different sides of a transparent substrate, which is good in cases when the one HOE interfere the other due to them being placed on top of each other.

According to some embodiments, the first HOE and the second HOE are placed next to each other on a transparent substrate, keeping the HOEs from interfering each other.

According to some embodiments, the at least one illuminators illuminate the eye via the HOE(s). In case with a hoe that is adapted to split the light, the light from each illuminator will be split into two and produce two glints in the eye. The reflection will then be split again and the image module can record four overlapped images, further enhancing accuracy of the depth calculation.

According to some embodiments, the at least one illuminator emit a wavelength in the rage of 700-1000 nm, i.e. in the near infrared (NIR), which is just above the visible spectra of the human eye so that user is not disturbed by the illuminators, but close enough to get a "red-eye" effect in the image captured by the image module, i.e. a strong reflex from the pupil of the eye. Identifying the pupil of the eye in the image is then very easy.

According to some embodiments, the first wavelength is in the range of 700-900 nm, preferably around 850 nm; and the second wavelength is in the range of 900-1000 nm, preferably around 940 nm. Both of the wavelengths are thereby well separated, while still in the NIR.

According to some embodiments, the difference between first angle and second angle is in the range of 1-20 degrees, preferably 2-10 degrees, more preferably 3-8 degrees, most preferably 4-6 degrees. The angle separation should be large enough to make a good depth calculation, but small enough to not waste resolution of the image module.

According to some embodiments, the at least one illuminator is illuminating in the direction of the viewing angle of the image module. According to some embodiments, the at least one illuminator is placed adjacent to the image module to save space and use basically the same optical path as the image module.

According to some embodiments, the at least one illuminator and the image module are separated by a beam splitter to virtually be placed in the same optical spot but still physically separated.

According to some embodiments, wherein the image module is angled to match the tilted focal plane produced by the optical setup with the HOE so as to remove the optical distortion caused by the angles of the incident light on the image module. The sensor is angled to match the tilted focal plane. This is the Scheimpflug principle to align focal plane and optically reduce distortion of the image.

According to some embodiments, wherein the eye tracking device is integrated into glasses, wherein the image module and the at least one illuminator are integrated into the frame of the glasses and the HOE or HOEs are placed on the glass portion of the glasses.

According to some embodiments, the eye tracking device further comprises a display placed in the glass portion of the glasses to look through for AR application or look at for VR applications.

Effects and features of the second and third aspects are largely analogous to those described above in connection with the first aspect. Embodiments mentioned in relation to the first aspect are largely compatible with the second aspect and third aspects. It is further noted that the inventive concepts relate to all possible combinations of features unless explicitly stated otherwise.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a", "an", "the", and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTIONS OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
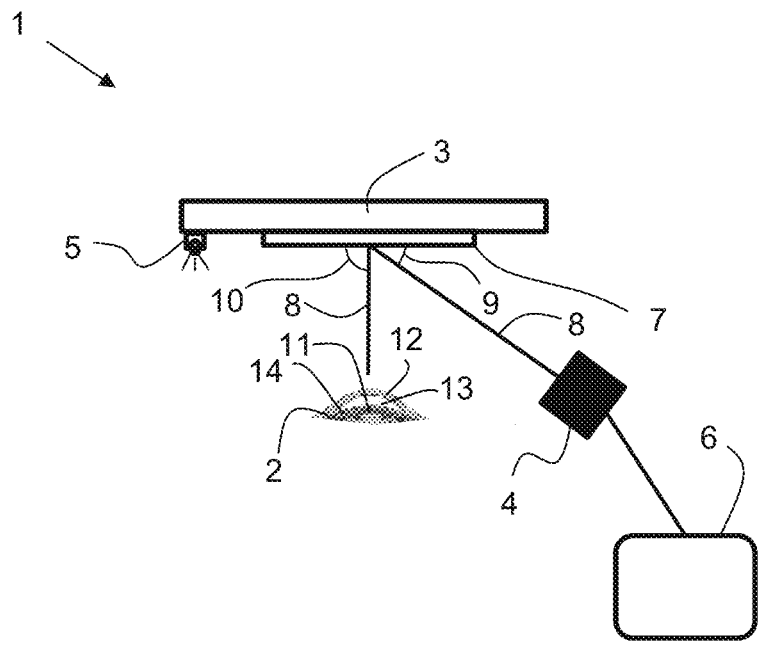
FIG. 1 is a schematic illustration of the eye tracking device with one HOE with illuminators illuminating the eye directly.

FIG. 1 shows an eye tracking device 1 for tracking movements of an eye 2 comprising, a viewing plane 3 for displaying a projection of an image to the eye 2 of a user. An image 4 module is placed on a same side of the viewing plane as the eye 2. At least one illuminator 5 is provided for illuminating the eye 2, and a control unit adapted to receive an image captured by the image module and calculate a viewing angle of the eye is provided connected to the image module 4. A holographic optical element HOE 7 is placed between the eye 2 and the viewing plane 3, wherein the image module is adapted to capture an image of the HOE 7, and wherein the HOE 7 is adapted to direct at last a first portion 8 of incident light reflected from the eye, in a first angle towards the image module, the first angle 9 being different from an angle of the incidence 10 of the incident light. The eye 2 has a pupil 11, a cornea 12, an anterior chamber 13 and an iris 14.

Figure 2:
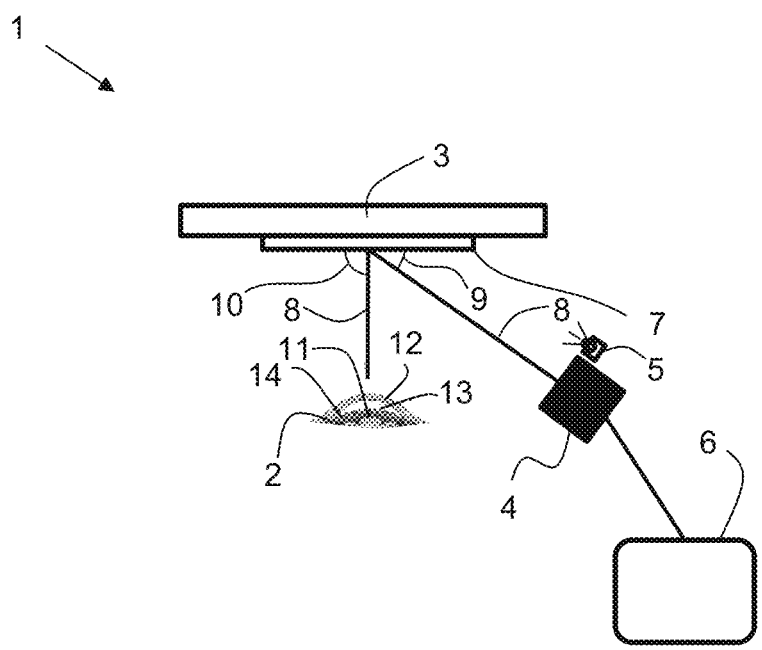
FIG. 2 is a schematic illustration of the eye tracking device with one HOE with illuminators illuminating the eye via the HOE.

FIG. 2 shows a similar embodiment as the one in FIG. 1, where the illuminator 5 is placed adjacent to the image module, illuminating the eye via the HOE 7.

Figure 3A:
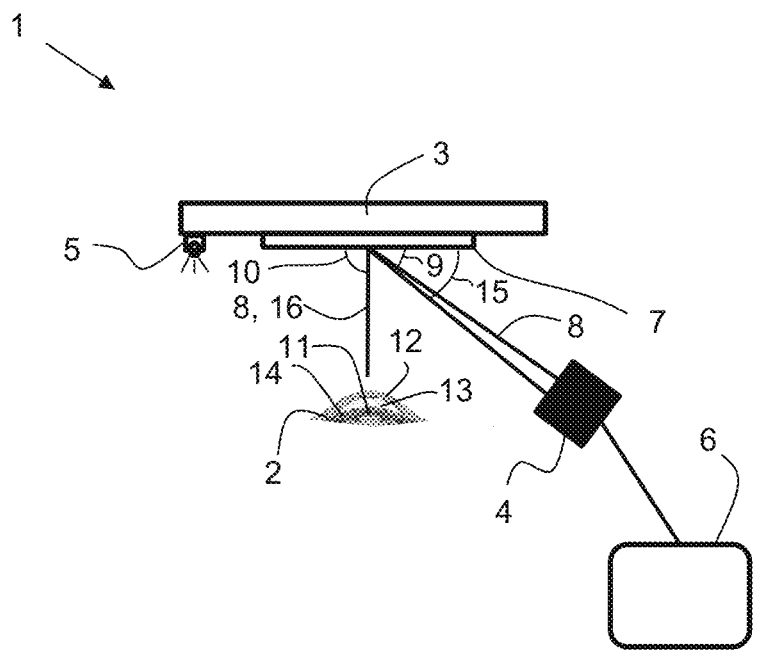
FIG. 3a is a schematic illustration of the eye tracking device with a HOE that splits incident light in two (angular multiplexing) and with illuminators illuminating the eye directly.
Figure 3B:
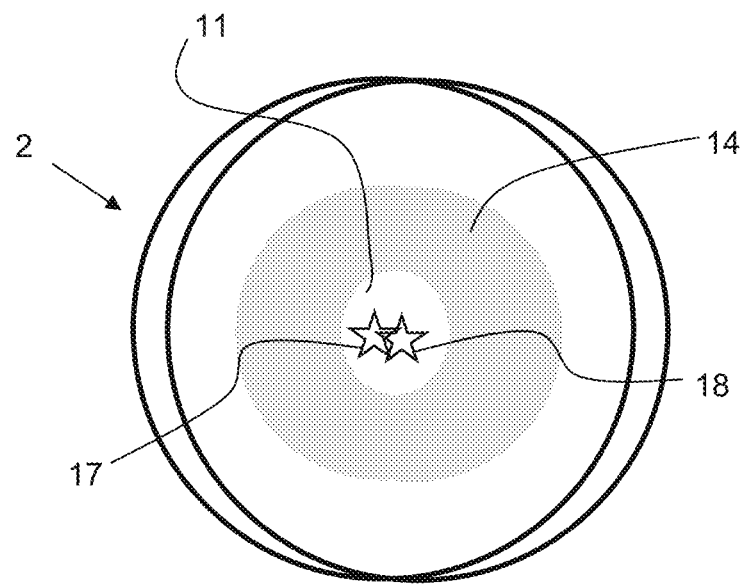
FIG. 3b is a schematic view of the eye of FIG. 3a and the glints in it from the illuminators.

FIG. 3a shows an embodiment where the first HOE 7 is adapted to direct a second portion 16 of incident light reflected from the eye in a second angle 15 towards the image module 4 enabling stereo imaging. FIG. 3b shows the image perceived by the image module 6 where two images are of the eye 2 are overlapped showing each having a glint refection 17, 18 of the illuminator 5. The image can be split into two by image analysis and compared to each other to determine the distance between the eye 2 and the HOE 7.

Figure 4A:
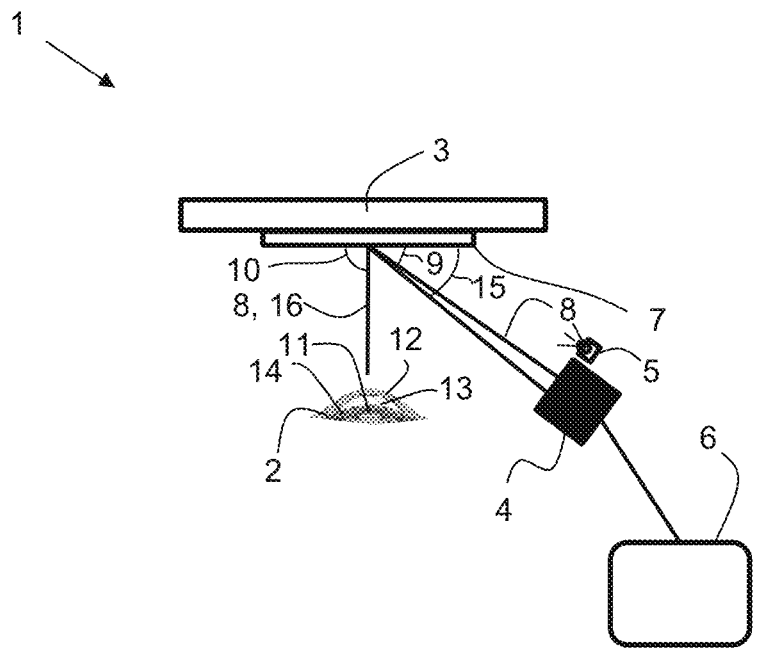
FIG. 4a is a schematic illustration of the eye tracking device with a HOE that splits incident light in two (angular multiplexing) and with illuminators illuminating the eye via the HOE.
Figure 4B:
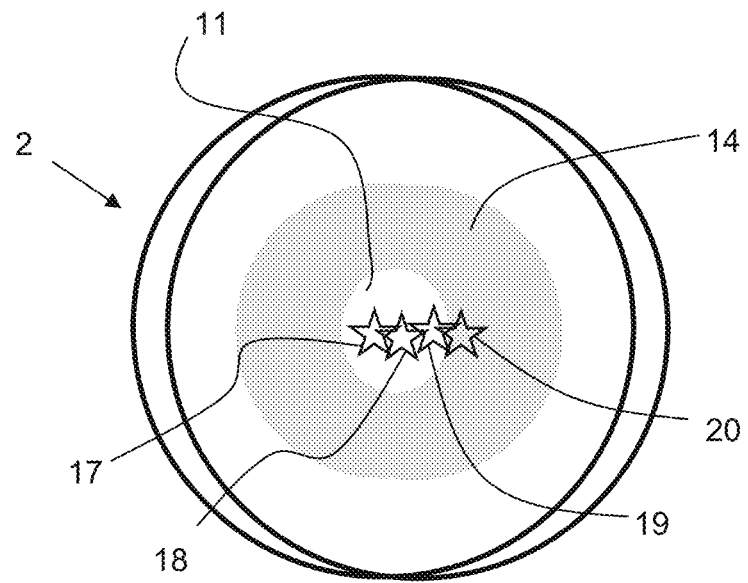
FIG. 4b is a schematic view of the eye of FIG. 4a and the glints in it from the illuminators.

FIG. 4a shows an embodiment where the illuminator 5 is placed adjacent to the image module 4 so that the eye 2 is illuminated via the HOE 7. The illumination is then split into two, i.e. the eye will see two illuminators. This will cause two reflections in the eye. The image module 4 will thereby capture an image with four glints 17, 18, 19, 20 in the eye 2 from one singe single illuminator 5 as shown in FIG. 4b. The increased information will produce a more accurate depth determination of the eye in relation to the viewing plane 3.

Figure 5:
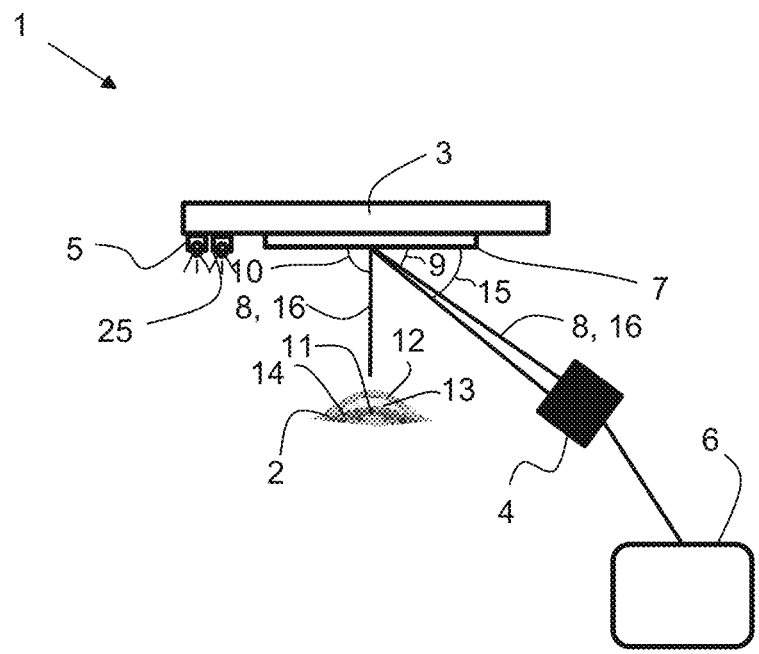
FIG. 5 is a schematic illustration of the eye tracking device with one HOE and two illuminators emitting different wavelengths.

FIG. 5 shows a schematic illustration of the eye tracking device with two illuminators 5, 25, with different wavelengths. The first portion of incident light 8 has a first wavelength and the second portion of incident light 16 has a second wavelength and a first illuminator 5 is emitting light of a first wavelength and the second illuminator 25 is emitting light of the second wavelength. The HOE 7 is preferably arranged to split the reflections from the illuminator in a wavelength dependent manner. If the image module 4 is color sensitive, the image can simply be color separated to split the two images and calculate the depth information.

Figure 6:
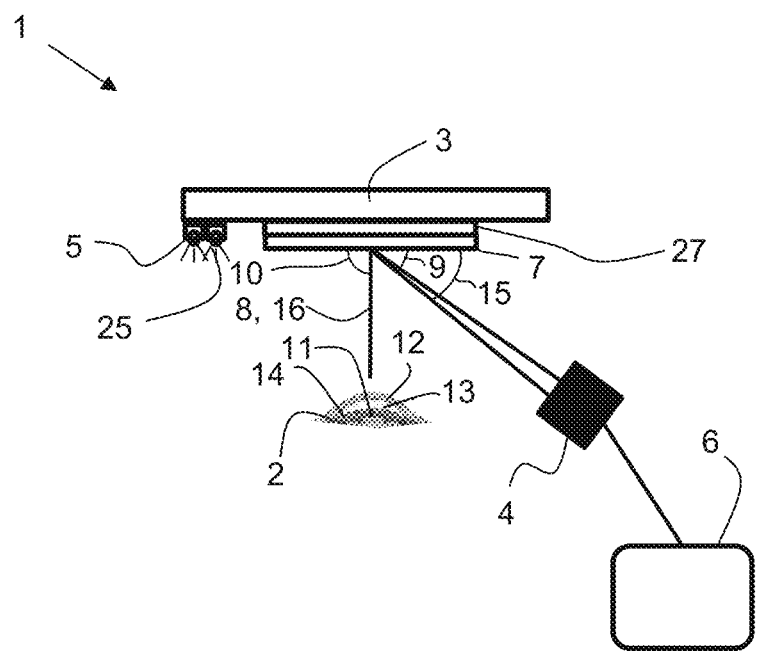
FIG. 6 is a schematic illustration of the eye tracking device with two HOEs and two illuminators emitting different wavelengths.

In FIG. 6 the embodiment of FIG. 5 is modified by introducing a second HOE 27, interposed with the first HOE 7. The second HOE 27 is adapted to direct incident light from the second illuminator 25 reflected from the eye in a second angle towards the image module. The first HOE 7 is adapted to direct light from the first illuminator 5 of the first wavelength but not the second wavelength and the second HOE 27 is adapted to direct light the second wavelength but not the first wavelength. The control unit is further adapted to control the illuminators such that only one illuminator is illuminating at the same time and such that one illuminator is illuminating the majority of the time.

According to some embodiments, the at least one illuminator 5 emit a wavelength in the rage of 700-1000 nm. The illuminator is preferably a LED. In the embodiment with a second illuminator 25, the first wavelength is in the range of 700-900 nm, preferably around 850 nm; and the second wavelength is in the range of 900-1000 nm, preferably around 940 nm. Both of the illuminator 5,25 thus emit light in the NIR.

Figure 7:
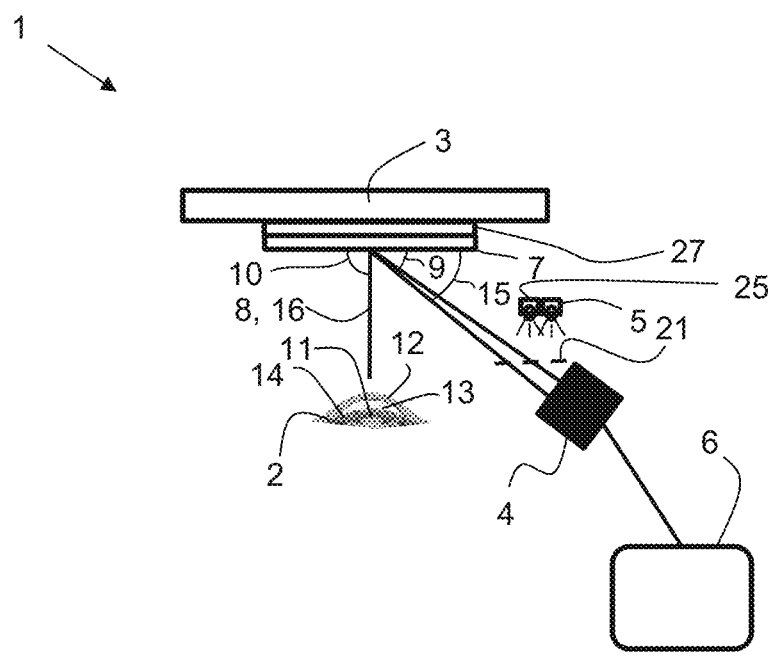
FIG. 7 is a schematic illustration of the eye tracking device with two HOEs and two illuminators with different wavelength, where a beam splitter is used for the illuminators.

FIG. 7 shows an embodiment where two illuminators 5, 25 and the image module 4 are separated by a beam splitter 21 so that the illuminator and the image module are virtually placed in the same optical spot.

Figure 8:
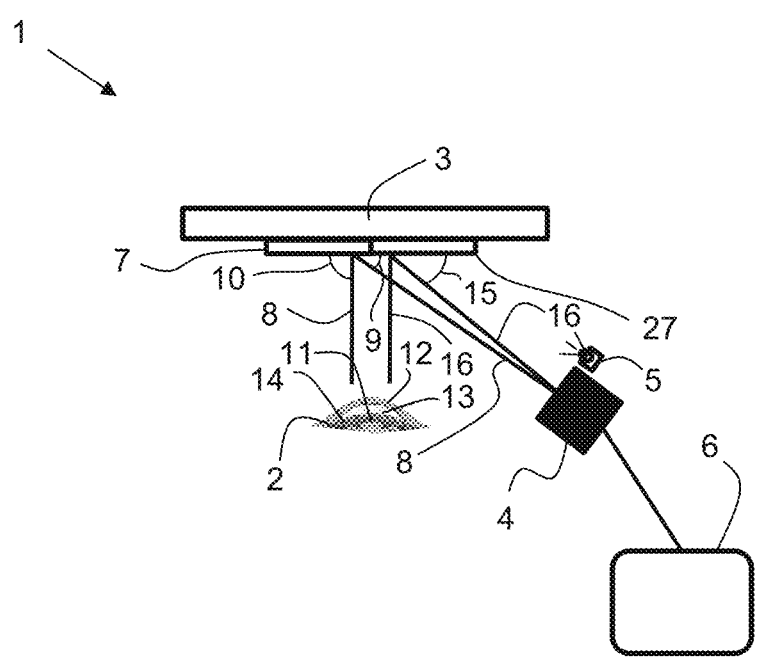
FIG. 8 is a schematic illustration of the eye tracking device with two HOEs placed beside each other on the substrate and one illuminator placed adjacent to the image module.

FIG. 8 shows an embodiment where a first illuminator 5 is placed adjacent to the image module 4 and where the eye tracking device comprises a first HOE 7 and a second HOE 27 placed adjacent to each other on the substrate 3. The first HOE 7 direct light from the illuminator reflected in the eye in a first angle towards the image module and the second HOE 27 direct light from the illuminator reflected in the eye in a second angle towards the image module.

Figure 9:
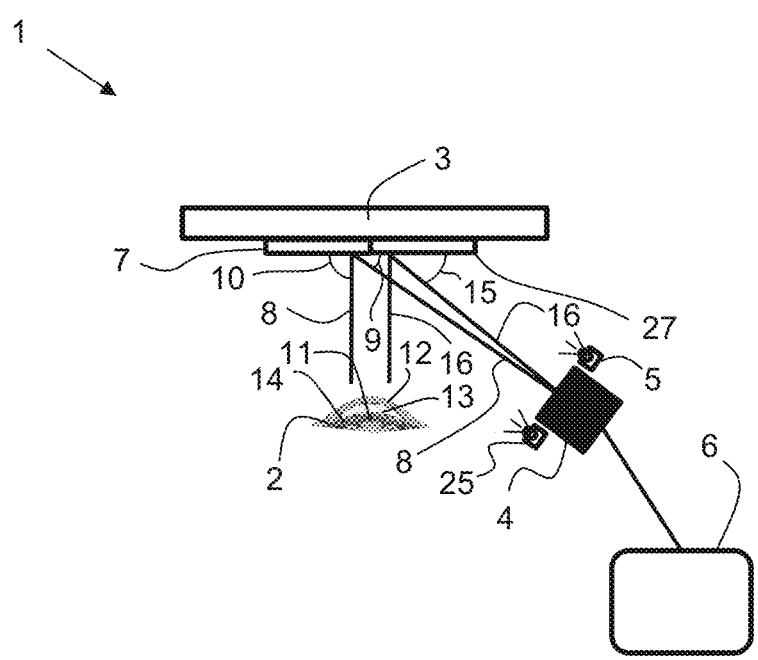
FIG. 9 is a schematic illustration of the eye tracking device with two HOEs for different wavelengths placed beside each other on the substrate and two illuminators emitting the two different wavelengths.

FIG. 9 shows an embodiment where two illuminators 5, 25 are placed adjacent to the image module 4 and where the eye tracking device comprises a first HOE 7 and a second HOE 27 placed adjacent to each other on the substrate 3. In that embodiment the illuminators preferably emit NIR light of different wavelengths. The first HOE 7 is adapted to direct light from the first illuminator 5 to the eye and reflections in the eye of the first illuminator 5 are directed back to the image module. The second HOE 27 is adapted to direct light from the second illuminator 25 to the eye and reflections in the eye of the second illuminator 25 are directed back to the image module. In that case the image separation is made on the sensor since they are imaged on different parts of the sensor, left-right or up-down.

According to some embodiments, the eye tracking device 1 is integrated into glasses (not shown).

The person skilled in the art realizes that the present invention by no means is limited to the preferred embodiments described above. On the contrary, many modifications and variations are possible within the scope of the appended claims.

For example, a person skilled in the art understands that the component shown in the embodiments of FIGS. 1-7 can be fit into the frame of glasses (not shown) where the image module 4 and the at least one illuminator 5, 25 are integrated into the frame of the glasses and the HOE 7 or HOEs 7, 27 are placed on the glass portion of the glasses; or that the eye tracking device may be integrated into other devices in need of eye tracking.

Additionally, variations to the disclosed embodiments can be understood and effected by the skilled person in practicing the claimed invention, from a study of the drawings, the disclosure, and the appended claims.

The invention claimed is:

1. An eye tracking device for tracking movements of an eye comprising,
 a viewing plane for displaying a projection of an image to the eye of a user,
 an image module placed on a same side of the viewing plane as the eye,
 at least one illuminator for illuminating the eye,
 a control unit adapted to receive an image captured by the image module, and calculate a viewing angle of the eye, a holographic optical element (HOE), wherein a HOE is placed between the eye and the viewing plane, wherein the image module is adapted to capture an image of the HOE, wherein the HOE is adapted to direct at last a first portion of incident light reflected from the eye, in a first angle towards the image module, the first angle being different from an angle of the incidence of the incident light; and wherein the HOE is adapted to direct a second portion of incident light reflected from the eye in a second angle towards the image module enabling stereo imaging.

2. The eye tracking device according to claim 1, wherein the first portion of incident light has a first wavelength and the second portion of incident light has a second wavelength, the eye tracking device further comprising a first illuminator emitting light of the first wavelength and a second illuminator emitting light of the second wavelength.

3. The eye tracking device according to claim 1, further comprising a second HOE wherein the second HOE is adapted to direct incident light reflected from the eye in a second angle towards the image module and a second illuminator for illuminating the eye, wherein the first illuminator and second illuminator irradiate light of a first wavelength and a second wavelength, respectively, and wherein the HOE is adapted to direct light the first wavelength but not the second wavelength and the second HOE is adapted to direct light the second wavelength but not the first wavelength.

4. The eye tracking device according to claim 2, wherein the control unit is further adapted to control the illuminators such that only one illuminator is illuminating at the same time.

5. The eye tracking device according to claim 4, wherein the control unit is further adapted to control the illuminators such that one illuminator is illuminating the majority of the time.

6. The eye tracking device according to claim 3, wherein the HOE and the second HOE are combined in a photo polymer layer.

7. The eye tracking device according to claim 3, wherein the HOE and the second HOE are placed on different sides of a transparent substrate.

8. The eye tracking device according to claim 3, wherein the HOE and the second HOE are placed next to each other on a transparent substrate.

9. The eye tracking device according to claim 1 wherein the at least one illuminators illuminate the eye via the HOE(s).

10. The eye tracking device according to claim 1, wherein the at least one illuminator emit a wavelength in the rage of 700-1000 nm.

11. The eye tracking device according to claim 2, wherein the first wavelength is in the range of 700-900 nm, preferably around 850 nm; and the second wavelength is in the range of 900-1000 nm, preferably around 940 nm.

12. The eye tracking device according to claim 1, wherein the difference between first angle and second angle is in the range of 1-20 degrees, preferably 2-10 degrees, more preferably 3-8 degrees, most preferably 4-6 degrees.

13. The eye tracking device according to claim 1, wherein the at least one illuminator is illuminating in the direction of the viewing angle of the image module.

14. The eye tracking device according to claim 1, wherein the at least one illuminator is placed adjacent to the image module.

15. The eye tracking device according to claim 13, wherein the at least one illuminator and the image module are separated by a beam splitter.

16. The eye tracking device according to claim 1, wherein the image module is angled to match the tilted focal plane produced by the optical setup with the HOE.

17. The eye tracking device according to claim 1, wherein the eye tracking device is integrated into glasses, wherein the image module and the at least one illuminator are integrated into the frame of the glasses and the HOE or HOEs are placed on the glass portion of the glasses.

18. The eye tracking device according to claim 17, further comprising a
display placed in the glass portion of the glasses.

* * * * *